(12) United States Patent
Mifsud

(10) Patent No.: US 11,366,087 B2
(45) Date of Patent: Jun. 21, 2022

(54) MICROPHONE COMPRISING GAS-MEASURING MEANS AND METHOD FOR MEASURING GAS BY MEANS OF SUCH A MICROPHONE

(71) Applicant: RUBIX S&I, Toulouse (FR)

(72) Inventor: Jean-Christophe Mifsud, Goudourville (FR)

(73) Assignee: RUBIX S&I, Toulouse (FR)

( * ) Notice: Subject to any disclaimer, the term of this patent is extended or adjusted under 35 U.S.C. 154(b) by 352 days.

(21) Appl. No.: 16/475,499

(22) PCT Filed: Dec. 19, 2017

(86) PCT No.: PCT/EP2017/083521
§ 371 (c)(1),
(2) Date: Jul. 2, 2019

(87) PCT Pub. No.: WO2018/127403
PCT Pub. Date: Jul. 12, 2018

(65) Prior Publication Data
US 2019/0346418 A1    Nov. 14, 2019

(30) Foreign Application Priority Data

Jan. 4, 2017   (FR) ...................................... 1750068

(51) Int. Cl.
*G01N 33/00*   (2006.01)
*A61B 5/08*    (2006.01)
(Continued)

(52) U.S. Cl.
CPC ......... *G01N 33/0036* (2013.01); *A61B 5/082* (2013.01); *G01N 33/497* (2013.01);
(Continued)

(58) Field of Classification Search
CPC .. G01N 33/0036; G01N 33/497; A61B 5/082; H04M 1/21; H04M 2250/12; H04R 1/028; H04R 2499/11
See application file for complete search history.

(56) References Cited

U.S. PATENT DOCUMENTS

| 2003/0094047 A1 | 5/2003 | Torkkeli | |
| 2016/0363572 A1* | 12/2016 | Blackley | ................ G01N 33/15 |
| 2016/0363582 A1* | 12/2016 | Blackley | ............. G01N 33/497 |

FOREIGN PATENT DOCUMENTS

| CH | 691 197 A5 | 5/2001 |
| JP | 2002-039981 A | 2/2002 |
| WO | WO 03/031968 A1 | 4/2003 |

OTHER PUBLICATIONS

Search Report on related FR application (FR 1750068) from the French Intellectual Property Office dated Jul. 28, 2017.
(Continued)

*Primary Examiner* — Tuan D Nguyen
(74) *Attorney, Agent, or Firm* — Klein, O'Neill & Singh, LLP

(57) ABSTRACT

Microphone comprising at least one perforated rigid membrane and at least one flexible membrane placed at a distance from the rigid membrane so as to form an enclosure between the rigid membrane and the flexible membrane, the flexible membrane being suited to being displaced by a sound vibration of air outside of the microphone via the perforated rigid membrane, said microphone being characterised in that it comprises means for measuring the quantity of at least one gas, said means for measuring being mounted in the enclosure in order to measure at least one gas present in said enclosure.

8 Claims, 3 Drawing Sheets

(51) Int. Cl.
    *G01N 33/497*    (2006.01)
    *H04M 1/21*    (2006.01)
    *H04R 1/02*    (2006.01)
    *H04R 1/08*    (2006.01)
(52) U.S. Cl.
    CPC .............. *H04M 1/21* (2013.01); *H04R 1/028* (2013.01); *H04R 1/08* (2013.01); *H04M 2250/12* (2013.01); *H04R 2499/11* (2013.01)

(56) References Cited

OTHER PUBLICATIONS

International Search Report and Written Opinion on corresponding PCT application (PCT/EP2017/083521) from International Searching Authority (EPO) dated Feb. 8, 2018.

* cited by examiner

MICROPHONE COMPRISING GAS-MEASURING MEANS AND METHOD FOR MEASURING GAS BY MEANS OF SUCH A MICROPHONE

TECHNICAL FIELD

The present invention relates to the field of the measurement of air and, more specifically, the breath of a person in order to measure the alcohol level, the hydration level, and/or the smell of the breath of a person.

Today, to measure the alcohol level in the breath of a user, a breathalyser comprises a gas sensor connected to a nozzle through which the user blows air. The gas sensor thus measures the quantity of alcohol present in the air blown out by the user. The breathalyser further comprises a flow meter to measure the flow rate of air blown out by the user and thereby to deduce therefrom the alcohol level.

In order to facilitate the use of the breathalyser, it is today known to link the breathalyser to a smart telephone known as a smartphone, in a wireless or wired manner. The user may thereby read the alcohol level measured by the breathalyser on the screen of the telephone.

However, such a breathalyser has drawbacks. Indeed, the breathalyser is an element independent of the telephone that the user thus always has to carry on him to measure his breath, which is bulky and increases the risk of forgetting or losing it.

One solution would be to integrate the breathalyser directly in a smartphone. However, the integration of a gas sensor and a flow meter necessitates providing an orifice in the telephone through which the user blows in order to make the air to measure pass through. Yet, dust and liquids can infiltrate inside the telephone through this orifice, which can damage it and thus represents a major drawback. In addition, the integration of a gas sensor and a flow meter in a smartphone, in which the available space is low, is complex and increases its cost.

In another field, a microphone comprising a sensor making it possible to measure the air pressure at the level of the microphone is known from the document US 2003/094047 A1. However, such a sensor does not make it possible to measure the level of a gas, and in particular the alcohol level in the breath of a user.

There thus exists a need for a gas sensor making it possible to measure in a reliable and efficient manner an alcohol level and, more generally the quantity of one or more gases, and which can be integrated in a practical manner and at lower cost in an electronic device, in particular, a telephone.

SUMMARY

To this end, the invention relates to a microphone comprising at least one perforated rigid membrane and at least one flexible membrane placed at a distance from the rigid membrane so as to form an enclosure between the rigid membrane and said flexible membrane, the flexible membrane being suited to being displaced by a sound vibration of air outside of the microphone via the perforated rigid membrane.

The invention is remarkable in that the microphone comprises means for measuring the quantity of at least one gas, said means for measuring being mounted in the enclosure in order to measure at least one gas present in said enclosure.

Thanks to the invention, it is possible to measure in a reliable and efficient manner the quantity of a gas by means of a microphone. Advantageously, the microphone thereby fulfils the twin function of measuring sounds and of measuring gases. Advantageously, an existing microphone may be adapted in order to integrate means for measuring. Such a microphone may be mounted in an electronic device instead of an existing microphone in order to enable said device to measure gases. Also, it is not necessary to provide a supplementary orifice in the electronic device, which limits the costs.

Preferably, the means for measuring are mounted on the flexible membrane, in particular by bonding, in order to be in contact with the air present in the enclosure. In addition, mounting by bonding makes it possible to assemble easily the means for measuring in the microphone during its manufacture. Such a positioning makes it possible to avoid modifying the perforated membrane and/or closing off the perforations. Advantageously, the addition of means for measuring only slightly affects the flexibility of the flexible membrane. Preferably, the means for measuring are mounted exclusively on the flexible membrane.

Alternatively, the means for measuring are mounted on the rigid membrane, in particular by etching on a membrane of the microphone, which makes it possible to limit the number of elements of the microphone and thereby to reduce the manufacturing and assembly costs. Preferably, the means for measuring are mounted exclusively on the rigid membrane.

According to a first embodiment, the means for measuring comprise at least one gas sensor comprising a layer sensitive to said gas to measure, said sensitive layer preferably being a metal oxide layer.

Preferably, the sensitive layer forms the flexible membrane of the microphone in order to limit the number of elements of the microphone and its cost. Moreover, this makes it possible to have available a large surface to measure gases. The gas sensor is thereby integrated in the microphone.

According to a second embodiment, the means for measuring comprise at least one gas chromatograph making it possible to measure separately the quantity of molecules of different gases.

The invention also relates to an electronic device, in particular a telephone, comprising a microphone such as described previously, suited, on the one hand, to measuring noises and sounds and, on the other hand, to measuring at least one gas in the air outside of the electronic device. Thus, the means for measuring can measure the gases in the air breathed out by the user when said user uses the electronic device, in particular a telephone.

The invention further targets a method for measuring, using a microphone such as described previously, the level of at least one gas in the air breathed out by a user, said method comprising:

A step of breathing out air by a user into said microphone,

A step of measuring, by the means for measuring of said microphone, the quantity of at least one gas in the air breathed out, A step of determining by the microphone the volume of air breathed out by the user, and A step of determining the level of the gas measured in the air breathed out from said measured quantity of gas and said determined volume of air breathed out.

Thus, the microphone makes it possible to measure the flow rate of air at the level of the means for measuring and does not require an additional flow meter, which limits the number of elements in the microphone and its cost. In addition, the measurement being made in the air breathed out by the user, this gesture is natural, which makes the use of the microphone easy for the user.

Advantageously, the volume of air breathed out is determined by measuring the pressure exerted by the air breathed out on the flexible membrane. The volume of air breathed out is thereby measured in a practical manner by measuring parameters characteristic to a microphone. The integration of the means for measuring in the microphone thus has synergies.

Preferably, the microphone being comprised in a telephone, the step of measuring the quantity of the gas in the air breathed out is carried out during a telephone call of the user.

Thus, a breath measurement may be carried out automatically without specific action of the user. A breath measurement is thereby non-intrusive and may be carried out in a frequent manner.

BRIEF DESCRIPTION OF THE DRAWINGS

The invention will be better understood on reading the description that follows, given uniquely as an example, and by referring to the appended drawings in which.

It should be noted that the figures display the invention in a detailed manner in order to implement the invention, said figures obviously being able to serve to better define the invention if needs be.

DETAILED DESCRIPTION

Figure 1:
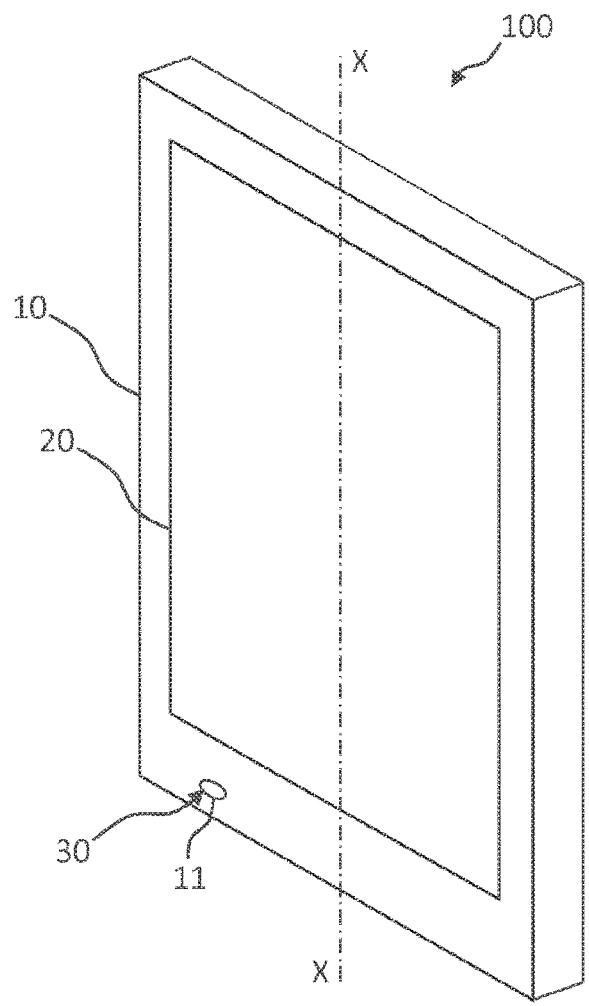
FIG. 1 is a schematic view of a mobile telephone comprising a microphone according to the invention.

With reference to FIG. 1, a mobile telephone 100 of the smartphone type is represented in a schematic manner. The mobile telephone 100 comprises a body 10, a display screen mounted on the body 10, a microphone 30 and an electronic system (not represented) suited to controlling the functions of the telephone.

In this example, the body 10 has a substantially parallelepiped shape extending longitudinally along an axis X-X so as to define a lower part in which is mounted the microphone 30 and an upper part in which is mounted a loudspeaker (not represented). The body 10 makes it possible to mount and to protect different elements of the telephone 100, such as the electronic system, a battery, etc. The body 10 also comprises two large faces, on one of which is mounted the screen 20.

The body 10 further comprises an orifice 11 in which is mounted the microphone 30. Preferably, the orifice 11 is placed at the level of the lower part of the telephone 100 so as to be near the mouth of the user when the user uses the telephone 100 to make a call. The orifice 11 enables the microphone 30 to be in contact with the air present outside of the telephone 100 in order to receive sounds, such as the voice of the user during a call, propagating through the air. Such a telephone is known by the person skilled in the art and will not be described in greater detail.

The telephone 100 comprises a microphone 30 according to the invention that will now be described.

Figure 2:
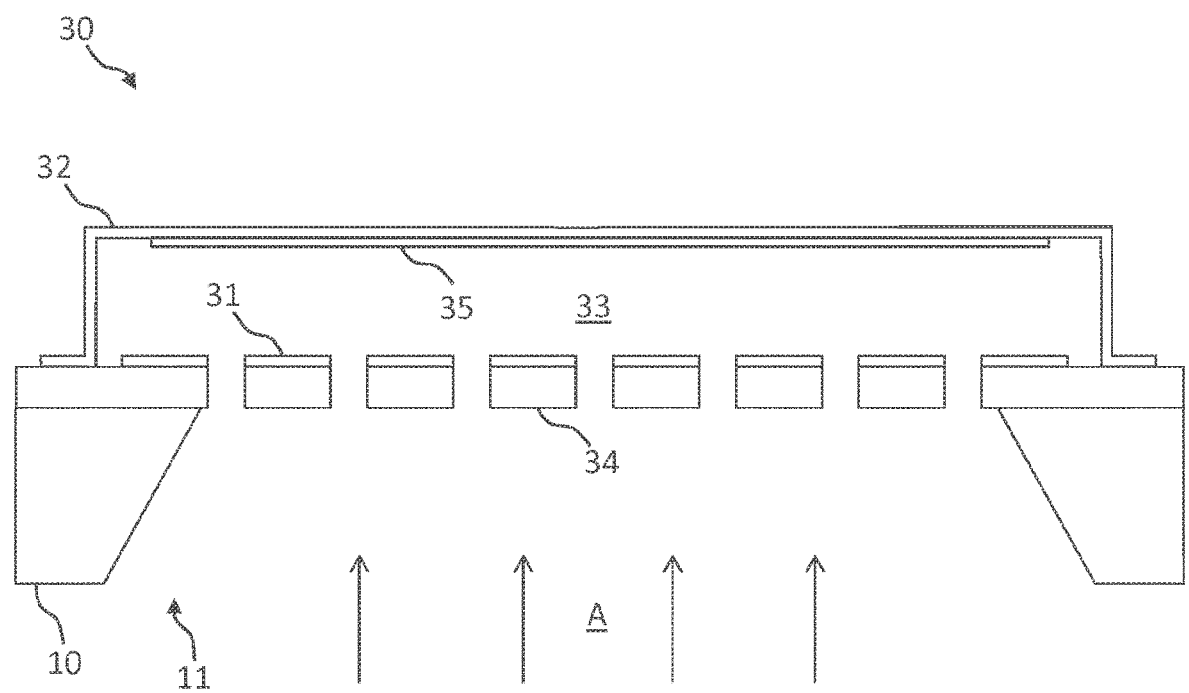
FIG. 2 is a schematic sectional view of a first embodiment of the microphone according to the invention.
Figure 4:
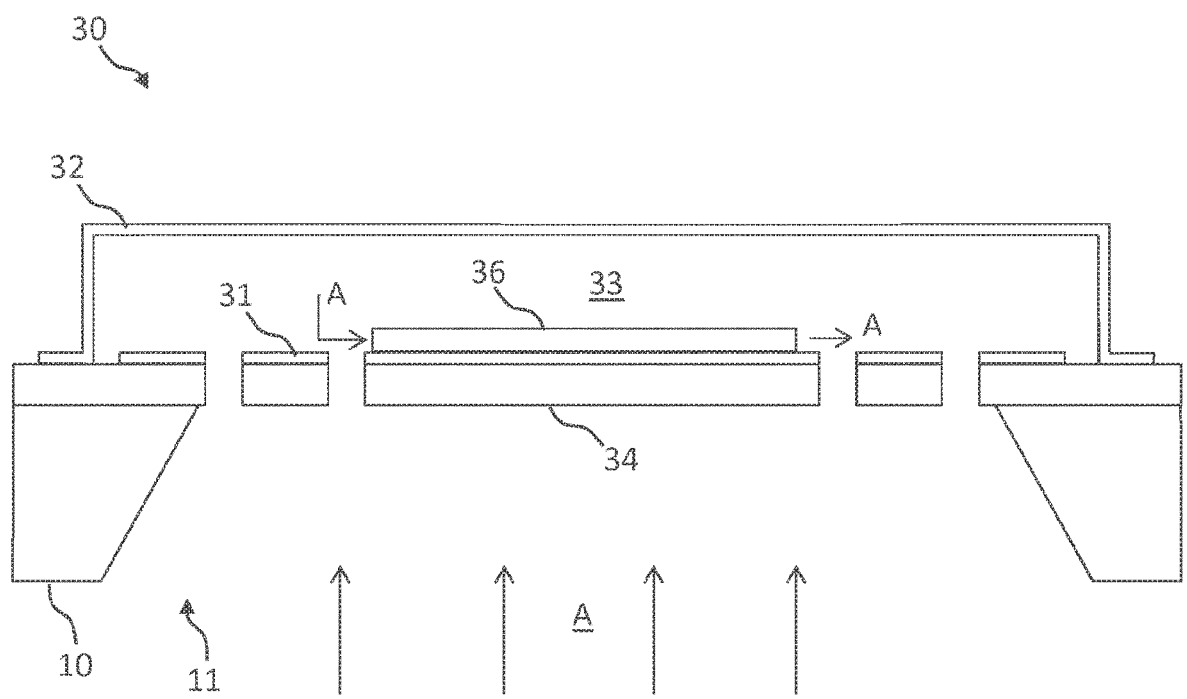
FIG. 4 is a schematic sectional view of a second embodiment of the microphone according to the invention.

With reference to FIGS. 2 and 4, a microphone 30 of MEMS (Micro Electrical Mechanical System) type is represented. The microphone 30 comprises a rigid membrane 31 and a flexible membrane 32 placed at a distance from the rigid membrane 31 so as to form an enclosure 33.

The rigid membrane 31 is perforated so that the enclosure 33 is fluidly connected to the air outside of the telephone A. Thus, a sound propagating in the outside air A propagates inside the enclosure 33 as illustrated in FIGS. 2 and 4.

The rigid membrane 31 may be made of silicon, ceramic or metal for example. The flexible membrane 32 is a thin membrane made of a composite material for example, suited to being deformed when the pressure exerted by the air A on the flexible membrane 32 varies. Preferably, the flexible membrane 32 comprises a cylindrical peripheral part extending orthogonally to the rigid membrane 31 and a flat part parallel to the rigid membrane 31 as illustrated in FIG. 2.

Advantageously, the microphone 30 according to the invention may be mounted instead of a microphone according to the prior art. The microphone 30 according to the invention is electrically connected to the electronic system in a manner analogous to the prior art, which makes its integration in the telephone 100 easy. Thus, the mounting of the microphone 30 does not require or requires little modification of the telephone 100, only the means for measuring have to be connected to the electronic system of the telephone 100.

In a known manner, when a sound propagates in the air A up to the microphone 30, the sound waves modify the pressure of the air A on the flexible membrane 32. Also, to measure a sound propagating in the air A, the microphone 30 measures the variation in the distance between the rigid membrane 31 and the flexible membrane 32 due to the sound waves.

To do so, the microphone 30 comprises a printed circuit 34 connected to the rigid membrane 31 and to the flexible membrane 32 so as to form a capacitor of which the capacitance varies according to the distance between the rigid membrane 31 and the flexible membrane 32. Thus, the microphone 30 transforms a sound into an electrical signal representative of said sound. The microphone 30 is then suited to sending the electrical signal representative of the sound to the electronic system of the telephone 100 in order to be exploited. The operation of such a microphone being known, it will not be described in greater detail.

The microphone 30 according to the invention further comprises means for measuring suited to measuring at least one gas present in the air A, such as ethanol, acetone, etc. According to the invention, the means for measuring are mounted in the enclosure 33 of the microphone 30 in order to be in contact with the air A. Thus, the means for measuring do not require any additional orifice in the telephone 100. In addition, the means for measuring are protected in the enclosure 33, in particular from dust, impacts, etc.

Figure 3:
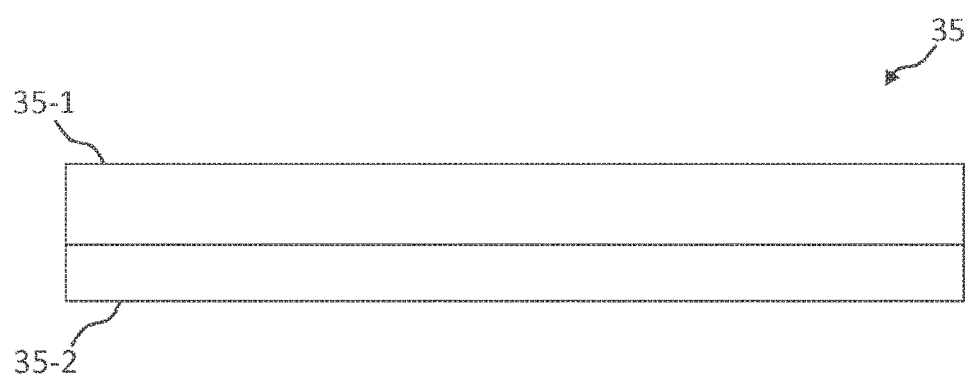
FIG. 3 is a schematic view of the means for measuring of the microphone of FIG. 2.

According to a first embodiment of the invention and with reference to FIGS. 2 and 3, the means for measuring comprise at least one metal oxide sensor 35, also designated MOS.

Such a MOS 35 comprises a layer sensitive 35-1 to at least one gas and a heating layer 35-2 mounted on said sensitive layer 35-1.

The sensitive layer 35-1 is in contact with the air A and is suited to absorbing molecules of the gas to measure. The absorption of these molecules varies the electrical conductivity through the sensitive layer 35-1 thanks to a redox reaction, which makes it possible to determine the quantity of said gas present in the air A in contact with the sensitive layer 35-1. In this case, the quantity of gas is measured from the variation in the resistance dR compared to the initial resistance Ro of the MOS 35. In other words, the quantity of gas measured is equal to the ratio dR/Ro.

The sensitive layer 35-1 comprises an oxide enabling a redox reaction with the gas, for example molecules of tin dioxide ($SnO_2$), titanium dioxide ($TiO_2$), tungsten trioxide ($WO_3$) and/or niobium oxide ($Ne_2O_5$) with dopings of elements of platinum (Pt), gold (Au), germanium (Ge) and/or palladium (Pd). The chemical elements that are mixed with the molecules making it possible to dope the latter in order to optimise their function of absorption of molecules of the gas to measure.

The heating layer 35-2 is commanded, preferably by the electronic system of the telephone 100, in order to modify the temperature of the sensitive layer 35-1, which enables the sensitive layer 35-1 to absorb different gases: each temperature of the sensitive layer 35-1 making it possible to measure the quantity of a gas. Thanks to the heating layer 35-2, a single sensitive layer 35-1 makes it possible to measure different gases, which makes it possible to limit the electrical energy consumption and the cost of the MOS 35. The heating layer 35-2 comprises in this example a substrate, such as ceramic or silicon, and elements, such as gold, suited to releasing heat when they are traversed by an electric current. The operation of an MOS 35 being known, it will not be described in greater detail.

According to the invention, the MOS 35 may be mounted on the rigid membrane 31 or instead on any part of the flexible membrane 32, in particular the wall and the flat part, on account of its flexibility compatible with the flexibility of the flexible membrane 32. Thus, the sensitive layer 35-1 is in contact with the air A present in the enclosure 33. The MOS may be mounted in the enclosure 33, for example by bonding of the heating layer 35-2 on the enclosure 33 in order that the sensitive layer 35-1 is in contact with the air A.

The means for measuring could also comprise more than one MOS 35. For example, MOSs of which the oxide is different in order to detect different elements of the gas to measure and thereby optimise this measurement. The MOS 35 may also be placed at different places: at least one first MOS 35 being able to be mounted on the flexible membrane 32 and at least one second MOS 35 being able to be mounted on the rigid membrane 31. This makes it possible in particular to carry out two measurements of the air A staggered over time in order to determine the difference in inertia between different molecules of the air A (the larger the dimensions of a molecule present in the air A, the more time it will take to be displaced between the two sensors), which makes it possible to optimise the detection of gas in the air A thanks to this additional parameter. The use of two MOSs 35 can also make it possible to use a first MOS 35 as a filter, in particular by increasing its temperature in order to burn certain gases, such as ethanol, and thereby enable the second MOS 35 to measure the different gases of the air without ethanol, which optimises the measurement.

In an alternative solution, the flexible membrane 32 is formed by the sensitive layer 35-1 of the MOS 35. In other words, the sensitive layer 35-1 of the MOS 35 is the flexible membrane 32 of the microphone 30 in order to minimise the number of elements in the microphone 30 and thereby to reduce the costs thereof. This also makes it possible to optimise the dimensions of the sensitive layer 35-1 and thereby to improve the measurement of gas.

In a preferred manner, the gas measuring means may implement selective detection technologies, for example based on carbon nanotubes, or non-selective, for example MOX technology.

Figure 5:
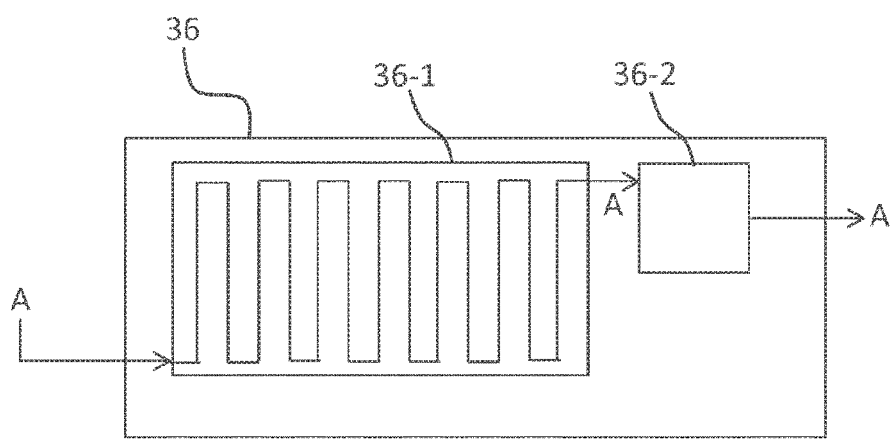
FIG. 5 is a schematic view of the means for measuring of the microphone of FIG. 4.

According to a second embodiment of the invention and with reference to FIGS. 4 and 5, the means for measuring comprise at least one gas chromatograph 36. Such a gas chromatograph 36 advantageously makes it possible to measure quantitatively a plurality of gases simultaneously. Preferably, the gas chromatograph 36 is mounted on the rigid membrane 31, for example by etching.

The gas chromatograph 36 comprises a column 36-1 and a gas detector 36-2 at the outlet of the column 36-1.

The air A of the enclosure 33 is injected into the column 36-1 when the user breathes out. The air A then traverses the column 36-1 comprising an absorbent solid, also designated stationary phase. In traversing the stationary phase, the gases comprised in the air A are separated on account of the different affinity of each gas with the stationary phase, which leads to a different propagation speed of each gas through the column 36-1. At the outlet of the column 36-1, the gases comprised in the air A being separated, the quantity of each gas comprised in the air A is then measured by the gas detector 36-2. Such a gas detector 36-2 may in particular be an etched thermocouple detector. The gas chromatograph 36 thereby makes it possible to measure the quantity of several gases present in the air A in an independent manner. The operation of such a gas chromatograph being known, it will not be described in greater detail.

Advantageously, the column 36-1 of the gas chromatograph 36 is etched on the rigid membrane of the microphone 30 in order to make its manufacture and its assembly easy.

In order to measure the quantity of a gas present in low quantity, the gas chromatograph 36 may also comprise a pre-concentrator at the inlet of the column 36-1. Such a pre-concentrator may in particular be of the activated carbon or Tenax type and is suited to capturing the molecules of a gas to measure then to release them in greater quantity at a certain temperature. The operation of the pre-concentrator being known, it will not be described in greater detail.

The means for measuring are electrically connected to the printed circuit 34 of the microphone 30 so that it collects the measured data. Advantageously, the printed circuit 34 comprises more connectors than a printed circuit according to the prior art to communicate with the electronic system of the telephone. In other words, it is uniquely necessary to adapt the number of connectors of the electronic system to receive the microphone according to the invention.

An exemplary embodiment of the method for measuring a gas according to the invention using a microphone 30 will now be described.

To measure his breath, the user blows air A towards the microphone 30. The air A then enters into the enclosure 33 up to the means for measuring which then measure the quantity of at least one gas representative of the breath of the user in the air A. In this example, the quantity measured is of the order of 0.02 grams. The means for measuring then send this measurement to the electronic system of the telephone 100 which can carry out computations directly or instead send them to a remote computer via a communication network in order that the computations are performed remotely.

Simultaneously, the microphone 30 measures the pressure that the blow of air A exerts on the flexible membrane 32 by measuring the variation in the distance between the rigid membrane 31 and the flexible membrane 32. In this example, the pressure is determined from the measurement of the variation in the pressure within the enclosure 33 when the user blows. Here, the measured variation is of the order of 10 hectopascals. This pressure is then sent to the electronic system of the telephone which determines the flow rate of air A blown by the user from the measured pressure and the surface area of the flexible membrane 31. Still in this example, for a surface area of 4 mm², the flow rate is then equal to 0.2 L/s. Then, the electronic system determines the volume of air A blown by the user from the determined flow rate and the time during which the user blows the air A. In this example, for a duration of 1 second, the volume of air A is equal to 0.2 L.

Then, the electronic system of the telephone 100 computes the level of gas in the air A from the quantity of this gas measured by the means for measuring and the determined volume of air A that the user has blown. In this example, for a quantity of 0.2 mg of gas and a volume of air A of 1 L, the level of the gas in the air A is 0.02 mg/L.

Advantageously, the measurement of the breath of the user may be carried out when said user makes a call. To do so, the user holds the telephone 100 vertically and places the telephone against his ear. The orifice 11 is then near the mouth of the user such that the air A entering into the enclosure 33 is the breath that the user breathes out while speaking. The means for measuring present in the enclosure 33 then measure the quantity of at least one gas representative of the breath of the user.

In speaking, the user also emits sound waves which propagate in the air A. These sound waves then pass through the perforated rigid membrane 31 of the microphone 30 in order to enter into the enclosure 33. The sound waves then vary the pressure at the level of the flexible membrane 32, which leads to a modification of the value of the capacitance of the capacitor formed by the rigid membrane 31 and the flexible membrane 32. The microphone then measures the pressure exerted by the air A on the flexible membrane and the duration during which this pressure is exerted in order to determine the flow rate of air A breathed out by the user. The variation in the capacitance further makes it possible to determine the emitted sound waves in order to transmit them to the interlocuter of the user.

From the measured quantity of the gas representative of the breath and the flow rate of the air A breathed out, the microphone determines the level of said gas representative of the breath in the air A breathed out.

Thanks to the microphone according to the invention, it is possible to measure the breath of a user of a telephone without additional holes in the telephone which makes it possible to protect the telephone. In addition, the integration of means for measuring in the microphone makes it possible to minimise the bulk of such means for measuring in a telephone as well as the cost thereof. Moreover, such an integration makes it possible to limit the infiltration of dust and liquids.

Advantageously, the microphone only comprises a single opening to enable the entry and exit of air.

Advantageously, the means for measuring gas make it possible to use technical means specific to the microphone, in particular, analogue-digital signal converting means. Since the technical means are pooled, the microphone obtained has a lower cost than an assembly comprising an independent microphone and an independent gas sensor.

Such a microphone may be used to measure the alcohol level of a person, to detect contamination of the ambient air, to analyse the breath of a person within the context of a medical diagnosis or to analyse the freshness of foodstuffs for example. Thanks to the microphone according to the invention, it is possible to create alerts in the event of abnormal measurements in the ambient air or in the breath of the user during his telephone calls. This makes it possible in particular to carry out a permanent monitoring of biomarkers present in the breath and which can be linked to the state of health of the user. These biomarkers may in particular be markers of fat consumption during physical exercises, markers of diabetes, lung cancer, tuberculosis, etc.

The measurement of a gas during a call has been described, but it goes without saying that the means for measuring could measure a gas in a continuous manner, in particular in the case of the detection of contamination of the ambient air in order to alert the user. The means for measuring could also carry out a measurement at the request of the user, in particular in the case of the analysis of the freshness of a foodstuff.

The microphone 30 according to the invention being connected to the electronic system of the telephone 100 in a similar manner to a microphone according to the prior art, it is possible to replace an existing microphone of a telephone by a new microphone according to the invention in order to obtain new functions, such as the measurement of the breath of the user.

A microphone 30 mounted in a telephone 100 has been described. But it goes without saying that the microphone 30 could be mounted in any other electronic device, in particular a music headset, headphones, a watch, an interphone, a vehicle, etc.

The invention claimed is:

1. A microphone comprising a perforated rigid membrane and a flexible membrane placed at a distance from the perforated rigid membrane so as to form an enclosure between the perforated rigid membrane and the flexible membrane, the flexible membrane being configured to being displaced by a sound vibration of air outside of the microphone via the perforated rigid membrane, said microphone comprises a metal oxide component mounted in the enclosure for measuring a quantity of gas, wherein the metal oxide component is sensitive to said at least one gas being measured, and wherein the metal oxide component forms the flexible membrane of the microphone.

2. The microphone according to claim 1, in which the metal oxide component for measuring is mounted on the flexible membrane.

3. The microphone according to claim 1, in which the metal oxide component for measuring is mounted on the rigid membrane.

4. The microphone according to claim 1, in which the metal oxide component for measuring comprises at least one gas chromatograph.

5. An electronic device comprising a microphone for measuring noises and sounds and for measuring at least one gas in the air outside of the electronic device, said microphone comprising a perforated rigid membrane and a flexible membrane placed at a distance from the perforated rigid membrane so as to form an enclosure between the perforated rigid membrane and the flexible membrane, the flexible membrane being configured to being displaced by a sound vibration of air outside of the microphone via the perforated rigid membrane, said microphone comprises a metal oxide component mounted in the enclosure for measuring a quantity of gas, wherein the metal oxide component is sensitive to said at least one gas being measured, and wherein the metal oxide layer forms the flexible membrane of the microphone.

6. A method for measuring a level of gas in the air breathed out by a user, said method comprising:
- a step of breathing out air by a user into a microphone, said microphone comprising:
  - a perforated rigid membrane and a flexible membrane placed at a distance from the perforated rigid membrane so as to form an enclosure between the perforated rigid membrane and the flexible membrane, the flexible membrane being configured to being displaced by a sound vibration of air outside of the microphone via the perforated rigid membrane, said microphone comprises a metal oxide component mounted in the enclosure for measuring a quantity of gas, wherein the metal oxide component is sensitive to said at least one gas being measured, and wherein the metal oxide layer forms the flexible membrane of the microphone;
- a step of measuring the quantity of at least one gas in the air breathed out;
- a step of determining, by the microphone, a volume of air breathed out by the user; and
- a step of determining the level of the at least one gas measured in the air breathed out from said measured quantity of the gas and said determined volume of air breathed out.

7. The method according to the claim 6, in which the volume of air breathed out is determined by measuring a pressure exerted by the air breathed out on the flexible membrane.

8. The method according to claim 6, in which, the microphone being part of a telephone, the step of measuring the quantity of gas in the air breathed out is carried out during a telephone call of the user in order to measure the level of gas in the air breathed out by the user during said call.

* * * * *